(12) United States Patent
Mühlhäusler et al.

(10) Patent No.: US 6,524,342 B1
(45) Date of Patent: Feb. 25, 2003

(54) SHOULDER ENDOPROSTHESIS

(75) Inventors: Bernd Mühlhäusler, Bad Suderode (DE); Diethard Wahl, Gosen (DE); Wilfried Glien, Bad Klosterlausnitz (DE); Dirk Salomon, Jonaswalde (DE)

(73) Assignee: Keramed Medizintechnik GmbH, Morsdorf (DE)

( * ) Notice: Subject to any disclaimer, the term of this patent is extended or adjusted under 35 U.S.C. 154(b) by 0 days.

(21) Appl. No.: 09/693,561

(22) Filed: Oct. 20, 2000

(30) Foreign Application Priority Data

Oct. 22, 1999 (DE) .................... 299 18 669 U

(51) Int. Cl.$^7$ ............................... A61F 2/40
(52) U.S. Cl. ................... 623/19.14; 623/22.45
(58) Field of Search ............ 623/19.11, 19.12, 623/19.13, 19.14, 23.15, 23.18, 23.44, 23.45, 23.46, 23.47, 22.45, 22.46

(56) References Cited

U.S. PATENT DOCUMENTS

| | | | |
|---|---|---|---|
| 5,507,817 A | 4/1996 | Craig et al. ............ 623/18 |
| 5,906,644 A | * 5/1999 | Powell ............... 623/20.15 |
| 6,090,146 A | * 7/2000 | Rozow et al. ........... 411/290 |
| 6,299,648 B1 | * 10/2001 | Doubler et al. ......... 623/22.42 |

FOREIGN PATENT DOCUMENTS

| | | | |
|---|---|---|---|
| DE | 36 05 630 A1 | 2/1986 | ....... A61F/2/28 |
| DE | 40 31 520 A1 | 5/1990 | ....... A61F/2/30 |
| DE | 19 54 81 54 A1 | 1/1992 | |
| DE | 19 84 16 12 A1 | 3/2000 | |
| DE | 19 84 16 11 A1 | 4/2000 | |
| EP | 01 27 503 A1 | 12/1984 | |
| EP | 02 78 807 A2 | 8/1988 | |
| EP | 02 78 807 B1 | 8/1988 | |
| EP | 01 27 503 B1 | 7/1989 | |
| EP | 06 79 375 B1 | 7/1989 | |
| EP | 03 29 854 A1 | 8/1989 | |
| FR | 2 666 221 | 4/1990 | ....... A61F/2/28 |
| FR | 2 664 809 A1 | 1/1992 | |
| FR | 2 735 972 | 12/1995 | ....... A61F/2/36 |
| WO | WO 99/34756 | 7/1999 | ....... A61F/2/40 |
| WO | WO 99/37254 | 7/1999 | ....... A61F/2/40 |

* cited by examiner

Primary Examiner—David J. Isabella
(74) Attorney, Agent, or Firm—Graybeal Jackson Haley LLP

(57) ABSTRACT

A shoulder endoprosthesis includes a middle section, a capitulum attachable to the middle section, and a shaft section adjustably attachable to the middle section. The middle section is adjustable relative to the shaft section along a shaft axis A of the shaft section and rotationally about the shaft axis A. The endoprosthesis also includes a clamping element for attaching the shaft section to the middle section.

10 Claims, 6 Drawing Sheets

SHOULDER ENDOPROSTHESIS

PRIORITY CLAIM

This application claims priority from German patent application No. 299 18 669.5, filed Oct. 22, 1999, which is herein incorporated by reference.

BACKGROUND OF THE INVENTION

1. Field of the Invention

This invention relates to a shoulder endoprosthesis comprising a capitulum, a middle section, to which the capitulum is attachable, and a shaft section, which is likewise attachable to the middle section.

2. Prior Art

The replacement of joints which are diseased or damaged through injury has for many years been part of daily practice in accident surgery and orthopaedics. In particular, artificial hip and knee joints have become firmly established in medicine.

In recent years, the replacement of damaged shoulder joints has also increasingly been carried out successfully.

The demands placed on artificial joints derive from the mechanical load placed on them, which occurs as an alternating load and must be borne over many years, as well as from the anatomical conditions to which the artificial joint must adapt, as well as from the environmental influences which the materials used must permanently resist.

Three material categories are basically used today to construct artificial joints. These are corrosion-resistant bio-tolerant metals; bio-compatible ceramics and plastics which satisfy the pertinent particular special mechanical requirements and the aging behaviour of which guarantees the ability of the joint to perform over many years.

Special problems which occur for joint endoprosthetics as a whole are the particular individual anatomical conditions to which the artificial joint must be adapted in order to reproduce, at least approximately, in the artificial joint the biomechanical and kinematic conditions which are present in the healthy joint.

Depending on the individual conditions, different sizes and designs of artificial joints are therefore manufactured to suit every application if at all possible. This is relatively easy in the case of hip joints, as the hip joint is a ball-and-socket-joint and, consequently is relatively easy to oversee in anatomical, biomechanical and kinematic terms.

The conditions in the knee joint are much more complicated, as the degrees of freedom of the knee joint are clearly limited by the combination of cap and ligament and sliding and rolling movements are superimposed on the natural joint.

Conditions are also relatively complicated in the shoulder joint, as the shoulder joint guarantees an exceptionally large degree of movement and the cavity (scapular glenoid cavity) covers only a small section of the capitulum.

Conditions become particularly difficult in the case of a joint destroyed by injury, as each individual case presents its own special problems. For this reason, shoulder prostheses are normally constructed modularly.

Thus there are many possible combinations which can be matched relatively well to the individual case.

However, this modularity also involves risks, which can primarily consist of reduced endurance or necessitate complicated connection mechanisms which complicate the operation technique and thus also increase the operation times.

A shoulder endoprosthesis with a shaft, a head neck section and a head cap is known from DE-A-195 48 154. The neck section is adjustable vis-à-vis the shaft so that the effective length of the shaft can be changed.

A shoulder endoprosthesis is known from EP-A 0 679 375 in which the middle section is adjustable vis-à-vis the shaft section in its rotation position about the shaft axis. The middle section is not adjustable along the shaft axis and the required length of the prosthesis is achieved by having middle sections of different lengths.

Also in the case of the shoulder endoprosthesis, which is known from FR-A 2 664 809, the length is likewise matched by intermediate pieces of different lengths.

A shoulder prosthesis is described in EP-B1-0 278 807 which consists of an upper arm piece and a piece bearing the ball-and-socket-joint. Both sections are movable lengthways against each other so that anatomical size ratios can be set. The rotation of the two sections against each other is however not fixed. Also anatomical angle ratios of the ball head to the humerus shaft cannot be set.

A shoulder prosthesis is known from DE-T2-38 76 087 which consists of a shaft section and a head section which are connected to each other via a cone plug connector. Very different anatomical conditions resulting from trauma cannot be taken into account with this prosthesis in either the head area or in the shaft area. Also, the angles are not settable.

A shoulder prosthesis is known from EP-B1-0 127 503 which consists of a humerus shaft and a joint cap. Head and shaft are switched in this prosthesis compared with the natural shoulder joint, so that the head section is attached to the shoulder blade. The advantage of the design is that it is luxation-resistant in all anatomical positions. However, this joint can be used only within limits, as it cannot be adapted to the various conditions, in particular in the case of traumatic indications. Moreover, the cavity section is very large and consequently cannot be implanted in anatomically favourable manner in every case.

SUMMARY OF THE INVENTION

The objective of the invention is a modularly constructed shoulder prosthesis which suits very differing anatomical conditions, in particular also traumatic indications.

The shoulder endoprosthesis of the invention comprises a capitulum, a middle section, to which the capitulum is attachable, and a shaft section, which is likewise attachable to the middle section, the middle section being adjustable vis-à-vis the shaft section along its shaft axis and in its rotation position about the shaft axis.

Preferably, the middle section has a bore and the shaft section can be clamped fast in this bore by means of a clamping element.

Preferably, the proximal end of the shaft section and the clamping element are provided with co-operating conical surfaces and the shaft section is clamped fast to the middle section by cone wedging.

The proximal end of the shaft section can be constructed as a conical bolt and the clamping element can be a spreadable or expandable sleeve with conical internal surface. By clamping the sleeve onto the conical bolt, the sleeve is expanded so that it is fixed in the bore of the middle section.

Another possibility is to provide the proximal end of the shaft with a conical bore and design it to be spreadable and to clamp a conical bolt into this bore as a clamping element so that the expanded end of the shaft section is fixed in the bore of the middle section.

The overall length of the prosthesis and the rotation angle between middle section and shaft section can be set by positioning the proximal end of the shaft section together with the clamping element that is still loosely seated on it inside the bore of the middle section.

Preferably, the overall length of the prosthesis is set continuously or in steps of less than 5 mm and the rotation angle between the middle section and shaft section is likewise set continuously.

Preferably, the middle section has an element for holding bone fragments. These can be claws or projections for the fixing of bone fragments.

According to the basic concept of the invention, the shoulder endoprosthesis is modularly constructed and consists of the shaft, the clamping element, the middle section and the capitulum. The connection of shaft and middle section can be adjusted continuously or in small steps in the axial direction of the shaft axis. The connection of shaft and middle section can also be continuously adjusted in its rotation angle about the shaft axis (ante- and retroversion angle). The connection of shaft and middle section is capable of absorbing rotation moments. The adjustment of the implant along the shaft axis and the rotation about it take place intraoperatively. These adjustments of the implant are carried out at the implanted shaft.

On the one hand, the sections of the shoulder prosthesis can thus be connected by simple and secure elements which can also still be exchanged during the operation, and on the other hand, the angular position and the effective length can be set continuously.

Through the modular construction, shafts can be used in different lengths and diameters, solid and modular heads with different external geometries can be used and the middle sections can be used with different external geometries. The head and middle sections can also be in one piece.

The shaft section and the middle section can be manufactured from titanium- or cobalt-chromium alloys and the capitulum from a cobalt-chromium alloy or ceramic.

BRIEF DESCRIPTION OF THE DRAWINGS

Embodiments of the invention are described in more detail below using the drawings. There are shown in.

DETAILED DESCRIPTION OF THE PREFERRED EMBODIMENTS

Figure 1:
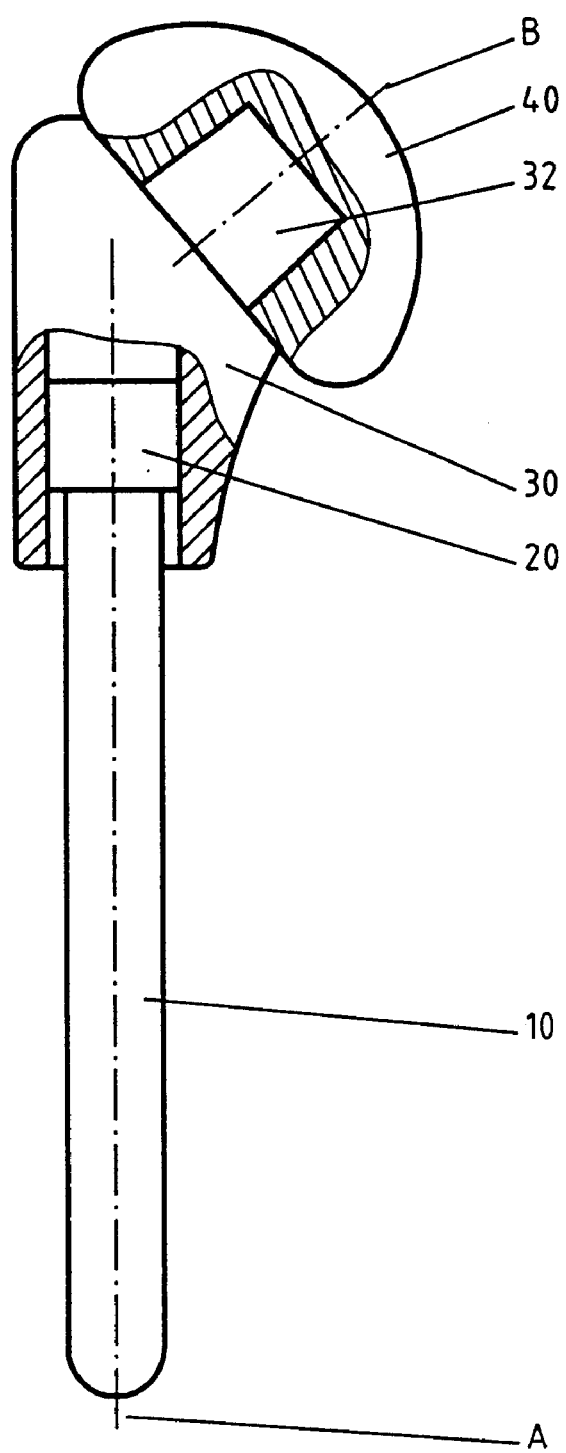
FIG. 1 the main structure and the function of the shoulder endoprosthesis.

The shoulder endoprosthesis in FIG. 1 has a shaft 10, a clamping element 20 fitted onto it, a middle section 30 fitted onto it and rotatable by 360° vis-à-vis the shaft axis A and height-adjustable along the shaft axis A. The middle section 30 has a seat or holder 32, the axis B of which is arranged askew or at an angle to the shaft axis A. The holder 32 serves to secure a head 40 of the shoulder endoprosthesis.

Figure 2:
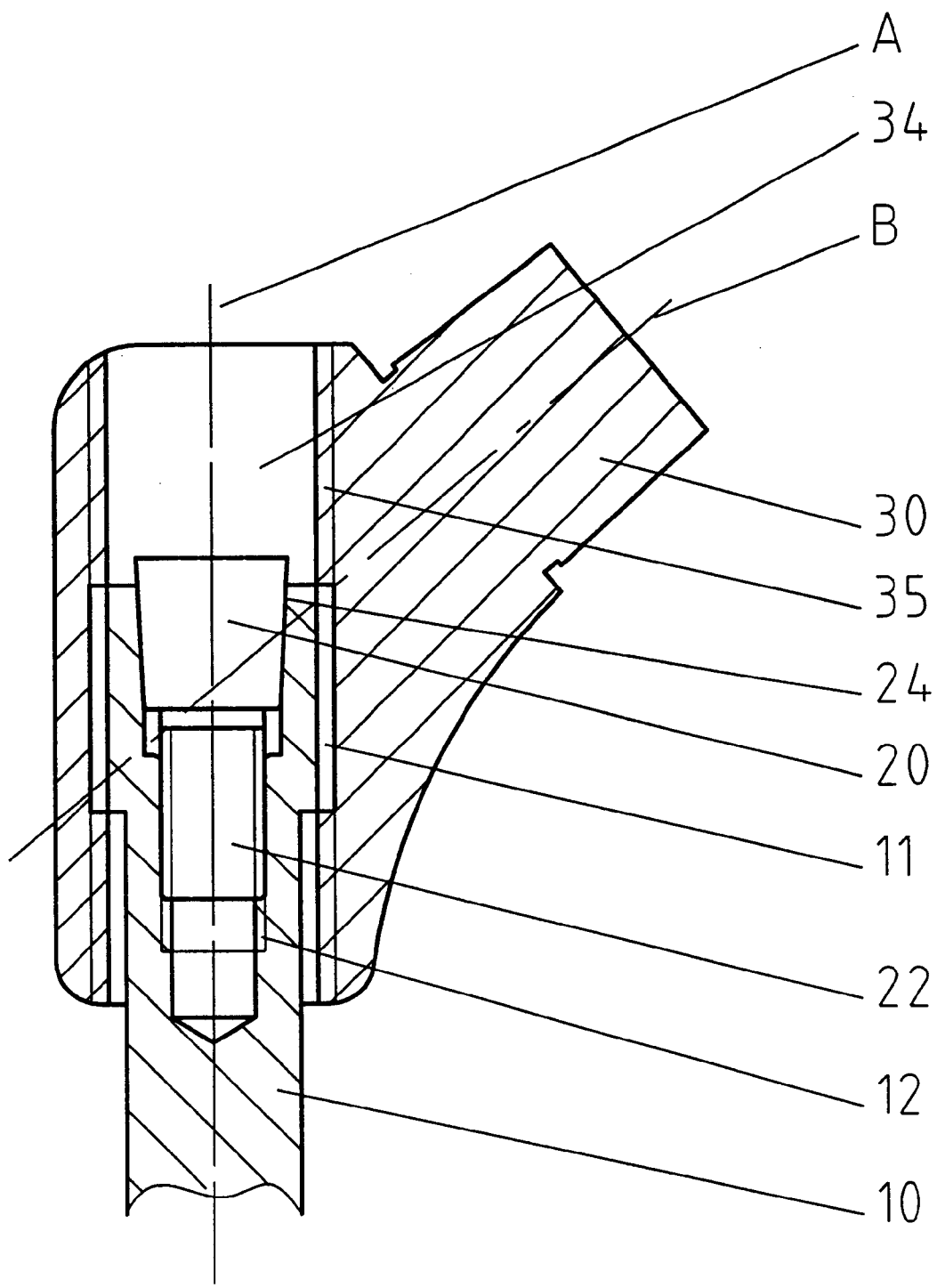
FIG. 2 in a sectional side view, the shoulder endoprosthesis without fitted ball with conical clamping element in the shaft and positive-locking connection to the middle section.

In the embodiment of FIG. 2, an expandable or spreadable external thread 11 and a threaded bore 12 are located at the proximal end of the shaft 10. The middle section 30 has a through bore 34 with internal thread 35. The middle section 30 with its internal thread 35 is screwed along the axis A onto the external thread 11 of the shaft 10. The clamping element 20 is formed by a threaded bolt 22 and a cone 24 attached to it. By screwing the threaded bolt 22 of the clamping element 20 into the threaded bore 12 in the proximal section of the shaft 10, the shaft 10 is fixed to the middle section 30 via the cone 24. The effective length of the shaft 10 can be changed by screwing the shaft 10 into the middle section 30 to different extents and be matched to the requirements of the particular case. After the shaft length has been set, the clamping element 20 is screwed in and the shaft 10 thereby clamped fast to the middle section 30. By unscrewing the clamping element 20, the clamping can also be loosened again during an operation in order to e.g. adjust the shaft length or the rotation position of the shaft 10.

Figure 3:
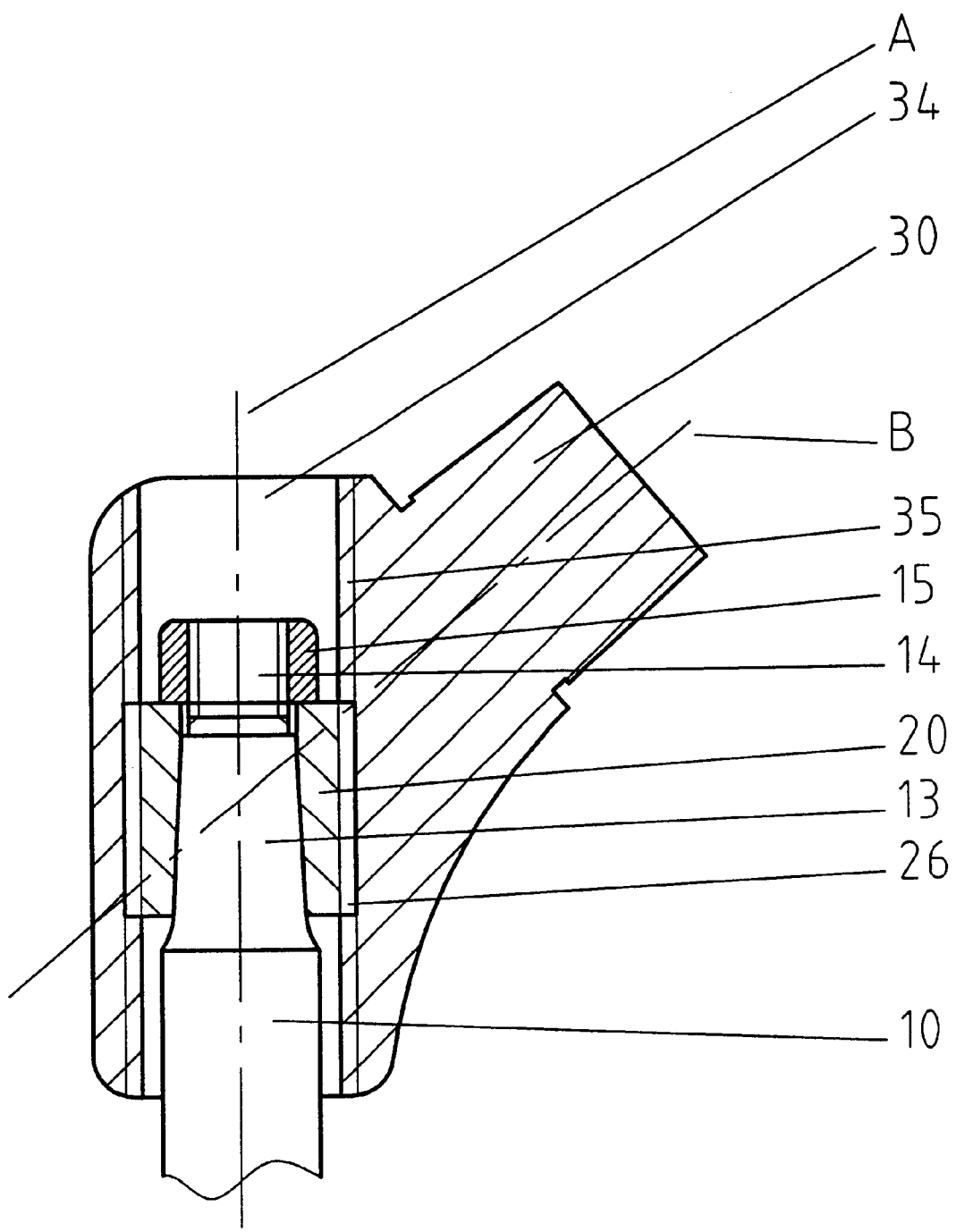
FIG. 3 in a sectional side view, the shoulder endoprosthesis without fitted ball with a sleeve-shaped clamping element and a securing screw and positive-locking connection to the middle section.

In the embodiment of FIG. 3, the proximal end of the shaft 10 is formed as a conical journal 13 ending in a threaded bolt 14. The clamping element 20 is an expanding sleeve with an internal diameter expanding conically in distal direction and with an external thread 26. The sleeve-shaped clamping element 20 is fitted onto the conical journal 13 and secured with a nut 15 and then screwed with its external thread 26 along the axis A into the middle section 30 until the shaft 10 has the desired effective length. By tightening the nut 15, the sleeve-shaped clamping element 20 is pressed against the conical journal 13 and thereby radially expanded, which leads to a bracing in the bore 34 of the middle section 30 and thus to a fixing of the length of the shaft 10. After the nut 15 is loosened again, an correction of the shaft length is possible.

Figure 4:
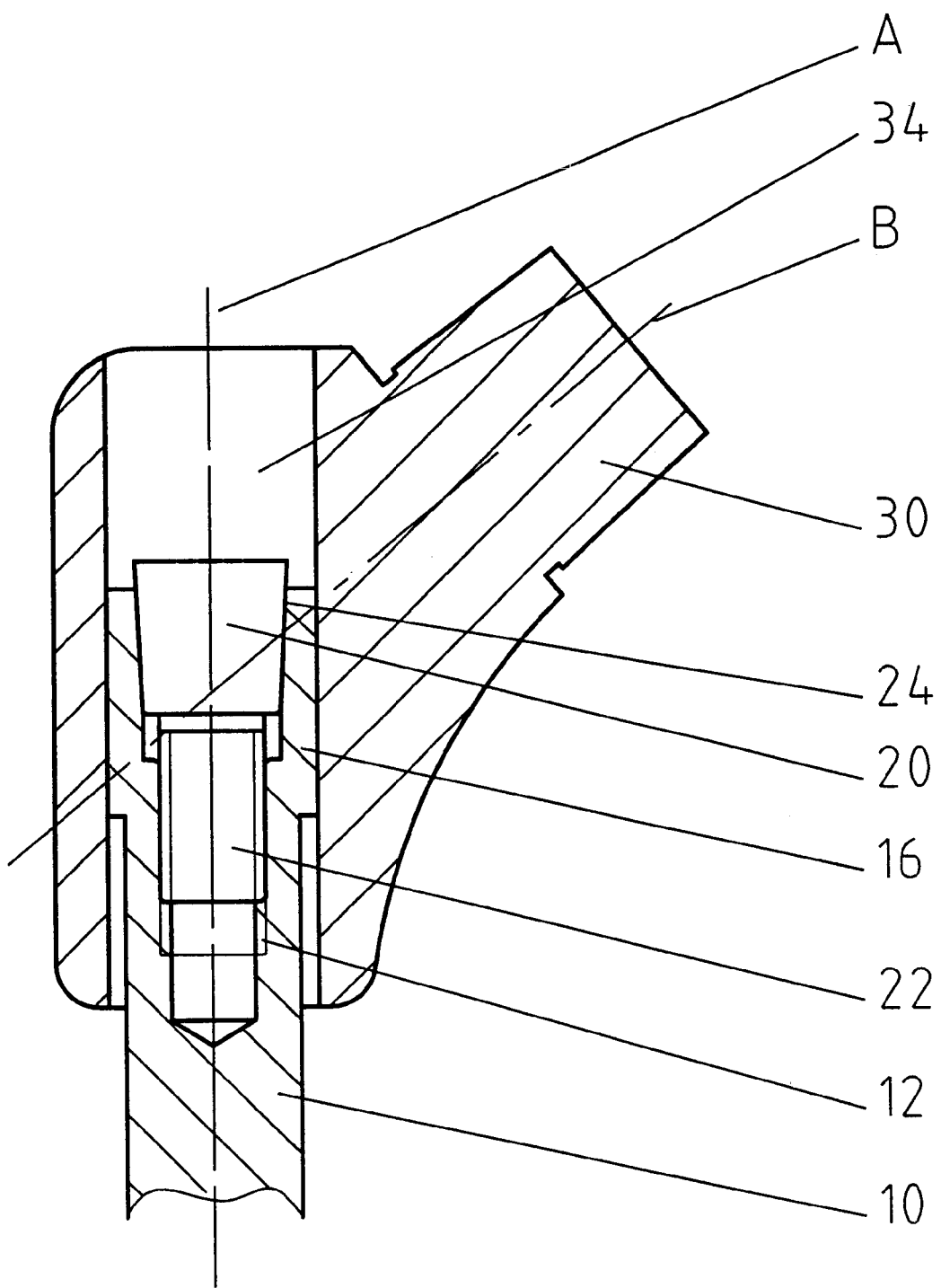
FIG. 4 in a sectional side view, the implant analogous to FIG. 2, but with friction-locking (non-positive) connection to the middle section.

The embodiment of FIG. 4 differs from that according to FIG. 2 in that the through bore 34 of the middle section 30 has a smooth internal wall instead of a thread. The shoulder endoprosthesis according to FIG. 4 thus consists of the shaft 10 at the proximal end of which an expandable or spreadable end piece 16 with smooth external surface is located. A threaded bore 12 is located in turn in the end piece 16. The middle section 30 with its inner bore 34 is fitted onto the end piece 16 of the shaft 10 along the axis A. The shaft 10 is fixed in the middle section 30 via the cone 24 by screwing the threaded bolt 22 of the clamping element 20 into the threaded bore 12.

Figure 5:
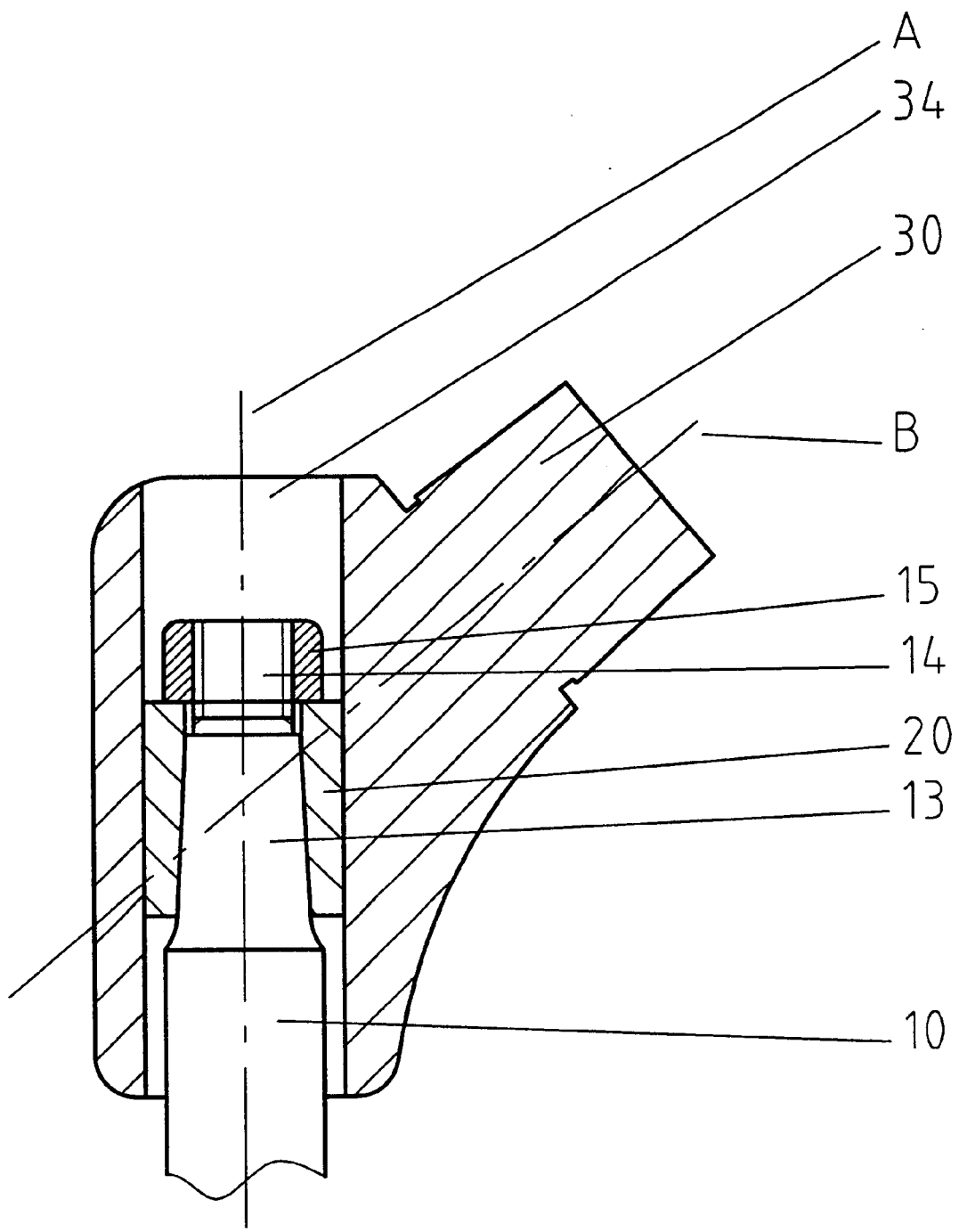
FIG. 5 in a sectional side view, the implant analogous to FIG. 3 but with friction-locking (non-positive) connection to the middle section and FIG. 6 a detail showing the securing of bone substance.

The embodiment of FIG. 5 likewise differs from that according to FIG. 3 only in that the through bore 34 of the middle section 30 has a smooth internal wall instead of a thread. In the embodiment of FIG. 5, the sleeve-shaped clamping element 20 is therefore fitted onto the conical journal 13 and the nut 15 is screwed on. The middle section 30 is then attached with its inner bore 34 along the axis A. By tightening the nut 15, the clamping element 20 is pressed onto the conical journal 13 and thereby expanded radially, which leads to a bracing in the bore 34 of the middle section 30.

Figure 6:
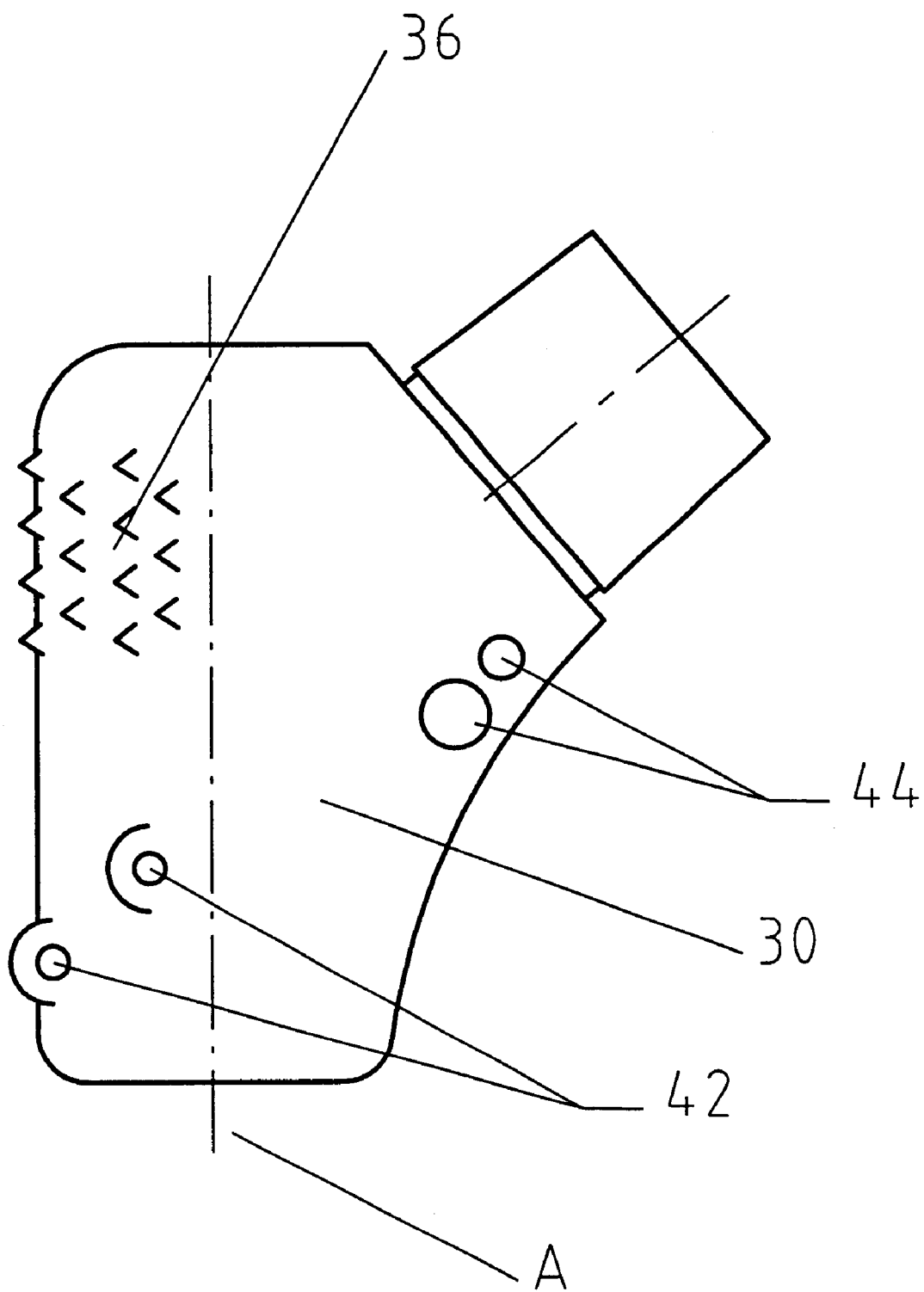

FIG. 6 shows the version of the middle section 30 with tipped projections 36. These are arranged proximally-laterally, in rows, in columns, diagonally or in any form such that bone fragments can be fixed in form-locking manner along the axis A against tensile forces by pressing onto these tipped projections. Attached to the distal end of the middle section of the prosthesis are bores 42 which permit a pulling-down and primary holding of the bone fragments over the tipped projections 36. Medially aligned bores 44 serve to hold threads which run over the proximally-laterally-pressed bone fragments and prevent their rising from the tipped projections 36. Furthermore, the tipped projections 36 are constructed such that the surface of the shoulder endoprosthesis and thus also the micration surface of the bone fragments is enlarged.

LIST OF REFERENCE LETTERS/NUMBERS

| | |
|---|---|
| A | shaft axis |
| B | holder axis |
| 10 | shaft |
| 11 | external thread |
| 12 | threaded bore |
| 13 | conical journal |
| 14 | threaded bolt |
| 15 | nut |
| 16 | end piece |
| 20 | clamping element |
| 22 | threaded bolt |
| 24 | cone |
| 26 | external thread |
| 30 | middle section |
| 32 | holder |
| 34 | bore |
| 36 | projections |
| 40 | capitulum |
| 42 | bore (at the distal end) |
| 44 | (medially aligned) bore |

What is claimed is:

1. A shoulder endoprosthesis having an overall length comprising:
   a middle section;
   a capitulum attachable to the middle section; and
   a shaft section adjustably attachable to the middle section and including a shaft axis, wherein the middle section is adjustable relative to the shaft section along the shaft axis to change the overall length continuously or in steps of less than 5 mm and about the shaft axis to change the rotational position of the middle section.

2. The shoulder endoprosthesis of claim 1, further comprising a clamping element for attaching the shaft section to the middle section, wherein the middle section includes a bore, and wherein, when the shaft section is attached to the middle section, the bore receives the shaft section and the shaft section receives the clamping element.

3. The shoulder endoprosthesis of claim 2, wherein the clamping element includes a cone that can be wedged in the bore of the middle section to attach the shaft section to the middle section.

4. The shoulder endoprosthesis of claim 3, wherein the shaft section includes a proximal end that is spreadable and includes a conical bore that receives the cone when the shaft section is attached to the middle section.

5. The shoulder endoprosthesis of claim 2, wherein the clamping element includes an expandable sleeve with a conical internal surface and the shaft section includes a proximal end having a conical external surface that contacts the conical internal surface when the shaft section is attached the middle section.

6. The shoulder endoprosthesis of claim 2, wherein the bore of the middle section includes an internal thread and the clamping element includes a corresponding external thread, and wherein, when the shaft section is attached to the middle section, the internal thread contacts the external thread.

7. The shoulder endoprosthesis of claim 2, wherein the bore of the middle section includes an internal thread and the shaft section includes a proximal end having a corresponding external thread, and wherein, when the shaft section is attached to the middle section, the internal thread contacts the external thread.

8. The shoulder endoprosthesis of claim 2, wherein the bore of the middle section includes a smooth internal surface and the clamping element includes a smooth external surface, and wherein, when the shaft section is attached to the middle section, the internal surface contacts the external surface.

9. The shoulder endoprosthesis of claim 2, wherein the bore of the middle section includes a smooth internal surface and the shaft section includes a proximal end having a smooth external surface, and wherein, when the shaft section is attached to the middle section, the internal surface contacts the external surface.

10. Shoulder endoprosthesis of claim 1, wherein the middle section includes an external surface and an element for securing bone fragments on the external surface.

* * * * *